(12) United States Patent
Lin

(10) Patent No.: US 10,376,252 B2
(45) Date of Patent: Aug. 13, 2019

(54) METHODS OF REPAIRING ABDOMINAL WALL DEFECTS

(71) Applicant: Dian-Yu Lin, Taipei (TW)

(72) Inventor: Dian-Yu Lin, Taipei (TW)

( * ) Notice: Subject to any disclaimer, the term of this patent is extended or adjusted under 35 U.S.C. 154(b) by 183 days.

(21) Appl. No.: 15/672,508

(22) Filed: Aug. 9, 2017

(65) Prior Publication Data

US 2019/0046171 A1 Feb. 14, 2019

(51) Int. Cl.
*A61B 17/00* (2006.01)
*A61F 2/00* (2006.01)
*A61B 17/04* (2006.01)

(52) U.S. Cl.
CPC .... *A61B 17/00234* (2013.01); *A61B 17/0057* (2013.01); *A61B 17/04* (2013.01); *A61F 2/0063* (2013.01); *A61B 2017/00238* (2013.01)

(58) Field of Classification Search
CPC ............ A61F 2/0063; A61F 2002/0068; A61F 2002/0072; A61B 17/00234; A61B 17/04; A61B 17/0057; A61B 2017/00238
See application file for complete search history.

(56) References Cited

U.S. PATENT DOCUMENTS

| | | | | |
|---|---|---|---|---|
| 5,269,753 A * | 12/1993 | Wilk | ................ | A61B 1/00082 600/109 |
| 5,383,477 A * | 1/1995 | DeMatteis | ......... | A61B 17/0057 128/898 |
| 5,607,441 A * | 3/1997 | Sierocuk | ............ | A61B 17/0218 600/207 |
| 5,911,726 A * | 6/1999 | Belknap | ........... | A61B 17/00234 606/144 |
| 9,510,926 B2 * | 12/2016 | Keane | ................ | A61B 17/0057 |
| 10,034,736 B2 * | 7/2018 | Blackburn | ............ | A61F 2/0063 |
| 2002/0103494 A1 * | 8/2002 | Pacey | ................... | A61F 2/0063 606/151 |
| 2010/0069930 A1 * | 3/2010 | Roslin | ................ | A61B 17/0057 606/151 |
| 2010/0179576 A1 * | 7/2010 | Halevy | ................ | A61F 2/0063 606/151 |
| 2011/0288568 A1 * | 11/2011 | Capuzziello | .......... | A61F 2/0063 606/151 |
| 2013/0066343 A1 * | 3/2013 | Park | ................... | A61B 17/3421 606/151 |
| 2014/0214079 A1 * | 7/2014 | Ewers | ................ | A61B 17/0401 606/232 |
| 2018/0049738 A1 * | 2/2018 | Meloul | ................ | A61B 17/068 |

* cited by examiner

*Primary Examiner* — Christopher L Templeton
(74) *Attorney, Agent, or Firm* — Muncy, Geissler, Olds & Lowe, P.C.

(57) ABSTRACT

The present invention provides a method of repairing a defect in an abdominal wall of a subject, including the steps of: making a small incision through a skin layer above the defect in the abdominal wall, introducing a surgical device including a deformable body through the incision to reach a preperitoneum underlying the abdominal wall around the defect, using the surgical device to identify a protruded region of the preperitoneum extending towards the abdominal wall around the defect, and flattening the protruded region of the preperitoneum and separating the protruded region of the preperitoneum from the abdominal wall with the deformable body in an expanded condition. The method results in low recurrence of abdominal wall defect, less pain, and a shorter hospital stay after surgery.

11 Claims, 11 Drawing Sheets

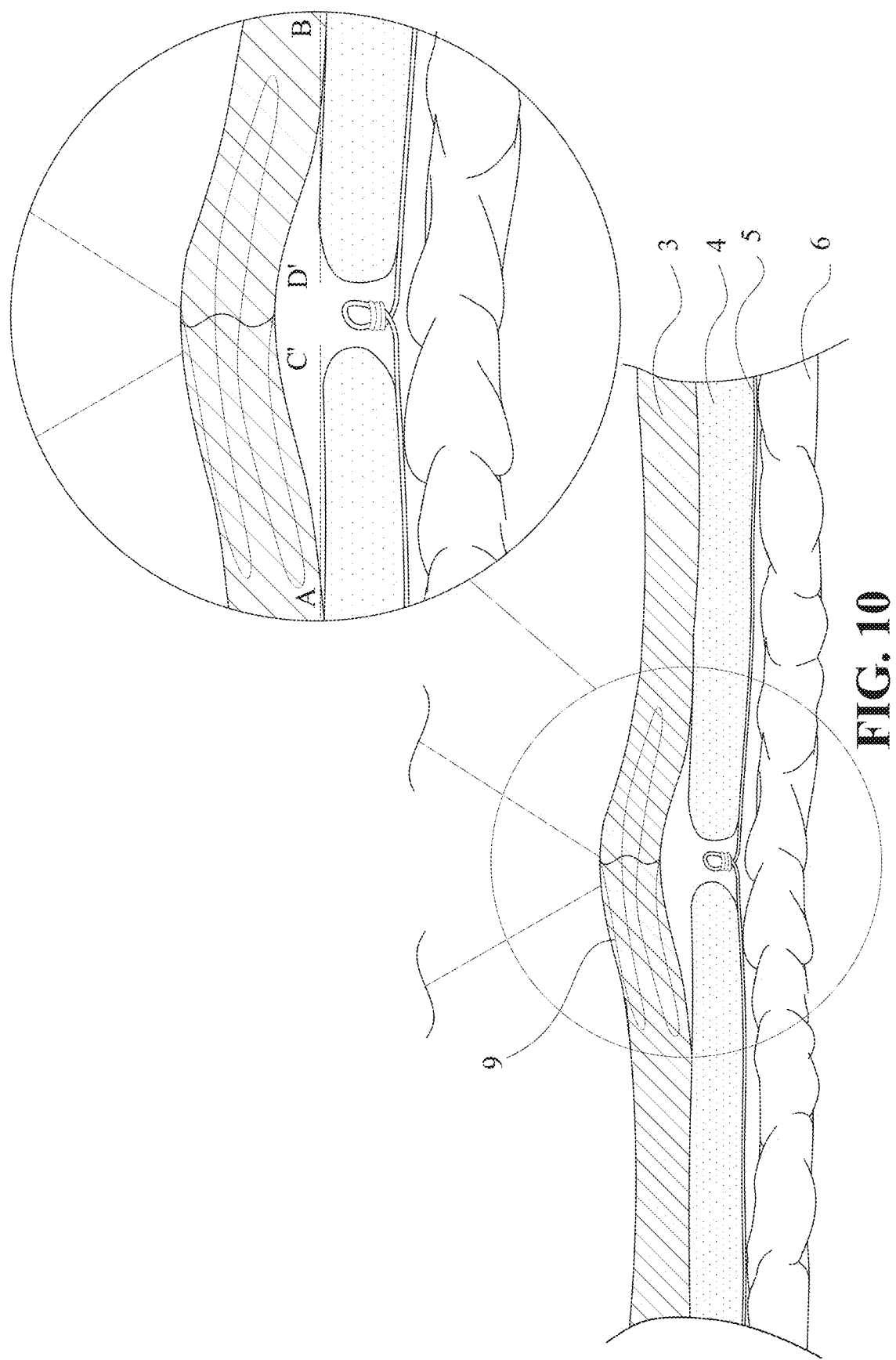

METHODS OF REPAIRING ABDOMINAL WALL DEFECTS

BACKGROUND OF THE INVENTION

1. Field of the Invention

The present invention relates to methods of repairing abdominal wall defects. Particularly, the present invention relates to methods of repairing abdominal wall defects using a surgical device including a deformable body to flatten preperitoneum protrusion surrounding the defects.

2. The Prior Arts

Defects in the abdominal wall usually occur at sites of weakness in the abdominal wall due to congenital factors and impaired muscles or connective tissues therein, and they may result in hernia when abdominal organs protrude through the defects. Many factors contribute to abdominal wall defects, including aging, obesity, long-term increased abdominal pressure caused by chronic constipation, benign prostatic hyperplasia, and sports. Though these defects may be repaired by surgery, factors such as malnutrition, infection, tension, and early return to unrestricted physical activities cause higher recurrence of hernia, leading to chronic pain in patients and increased difficulty in repairing the recurring defects.

Several types of methods for abdominal hernia repair are used by surgeons. For example, traditionally, surgeons may use the open hernia repair, suturing together the natural tissues around the defect or applying a surgical mesh to cover the defect, or the laparoscopic hernia repair, using a surgical mesh to repair the defect with laparoscopy. Both the open hernia repair, such as Bassini repair, Shouldice repair, and, Lichtenstein repair, and the laparoscopic hernia repair, such as totally extraperitoneal (TEP) repair and trans-abdominal preperitoneal (TAPP) repair, have low recurrence rates. However, for open hernia repair surgery, a quite large incision (about 6-12 cm) is required; for laparoscopic hernia repair surgery, one to three small incisions (about 1-3 cm) are usually required. Further, laparoscopic hernia repair is performed under general anesthesia, which increases surgery risks in elderly patients.

Therefore, there is an urgent need to develop a novel method of repairing the abdominal wall defects through a single small incision in order to achieve a low recurrence rate with less pain and high safety.

SUMMARY OF THE INVENTION

As a result, the present invention provides a method of repairing a defect in an abdominal wall of a subject, comprising the steps of: (a) making an incision through a skin layer above the defect in the abdominal wall, wherein the incision is smaller than the defect, (b) introducing a surgical device through the incision to reach a preperitoneum underlying the abdominal wall around the defect, wherein the surgical device includes a deformable body, (c) using the surgical device to identify a protruded region of the preperitoneum extending towards the abdominal wall around the defect, and (d) flattening the protruded region of the preperitoneum and separating the protruded region of the preperitoneum from the abdominal wall with the deformable body in an expanded condition.

In one embodiment, the incision is about 2-3 cm in length, and the subject is given local anesthesia prior to step (a).

In another embodiment, the surgical device further includes a monitoring element such as an endoscope; the deformable body is an inflatable sac.

In still another embodiment, the defect is a hernia defect, and the abovementioned method further includes the following steps: excising a hernia sac within the defect prior to step (b), suturing continuously between a plurality of tissues in proximity to the defect in an overlapping manner, such as a three-dimensional overlapping manner, to reconstruct the abdominal wall after step (d), placing a surgical mesh, decided by surgeon depending on the conditions of the surrounding tissues (thickness, elasticity, metabolism of the subject), between the abdominal wall and the flattened preperitoneum and suturing the surgical mesh to the abdominal wall, and finally closing the incision of the skin layer.

The method of the present invention is characterized by flattening the protruded region of the preperitoneum, separating the protruded region of the preperitoneum from the abdominal wall, and dissecting with the deformable body of the surgical device through a single small incision. This step, referred to as augmenting preperitoneum preparation or APP, provides the following benefits to the surgery. First, separation of the abdominal muscle wall from the protruded preperitoneum and underlying abdominal organs, and flattening of the preperitoneum to its natural position result in a wider, flattened preperitoneum. Second, from the posterior view of the abdominal wall, the APP widens the underlying space and length around the abdominal muscle wall, which allows the repaired abdominal muscle wall being sutured in a wider anchoring structure, providing better mechanical structure and supporting strength resistant to abdominal stress. Third, the APP performed with a monitoring element such as an endoscope provides a visible and systemic dissection and thus improves upon the blind dissection characteristic of the traditional anterior method of open hernia repair. Forth, in contrast to TEP repair, which requires general anesthesia, the APP provides an approach to develop preperitoneum space (Bogros space) in patients using local anesthesia with IV sedation. Fifth, the APP optimally provides a manner to measure the condition of natural tissue, allowing surgeon to decide whether to apply a mesh into Bogros Space. Also, the APP facilitates better extension and anchoring of the mesh to the abdominal muscle wall, leading to augmentation of the abdominal wall. Sixth, the APP separates the preperitoneum and the abdominal muscle wall originally adhering to each other and thus reduces the tension of the reconstructed abdominal wall, like closing the curtains layer by layer. The management of tension of the abdominal wall lowers postoperative pain and decreases the recurrence rate of abdominal defect.

The present invention is further explained in the following drawings and examples. It is understood that the examples given below do not limit the scope of the invention, and it will be evident to those skilled in the art that modifications can be made without departing from the scope of the appended claims.

BRIEF DESCRIPTION OF THE DRAWINGS

FIG. 10 is a cross-sectional view illustrating the increased space between the abdominal wall and the preperitoneum and the shorter cross-sectional length of a region of the preperitoneum when augmenting preperitoneum preparation is applied.

DETAILED DESCRIPTION OF THE PREFERRED EMBODIMENT

Definition

The term "augmenting preperitoneum preparation" and the abbreviation "APP" as used herein, refers to the action which flattens the protruded region of the preperitoneum surrounding a defect in the abdominal wall and separates the protruded region of the preperitoneum from the abdominal wall, so that no protrusion or bulge is present in the preperitoneum, and hence a space between the abdominal wall and the preperitoneum is created. This action is executed before reconstruction of the abdominal wall in the method of the present invention.

The present invention provides a surgical method to repair a defect such as a hernia defect in the abdominal wall of a subject. Inguinal hernia repair is described in the following as an example to illustrate the method of the present invention.

Figure 1A:
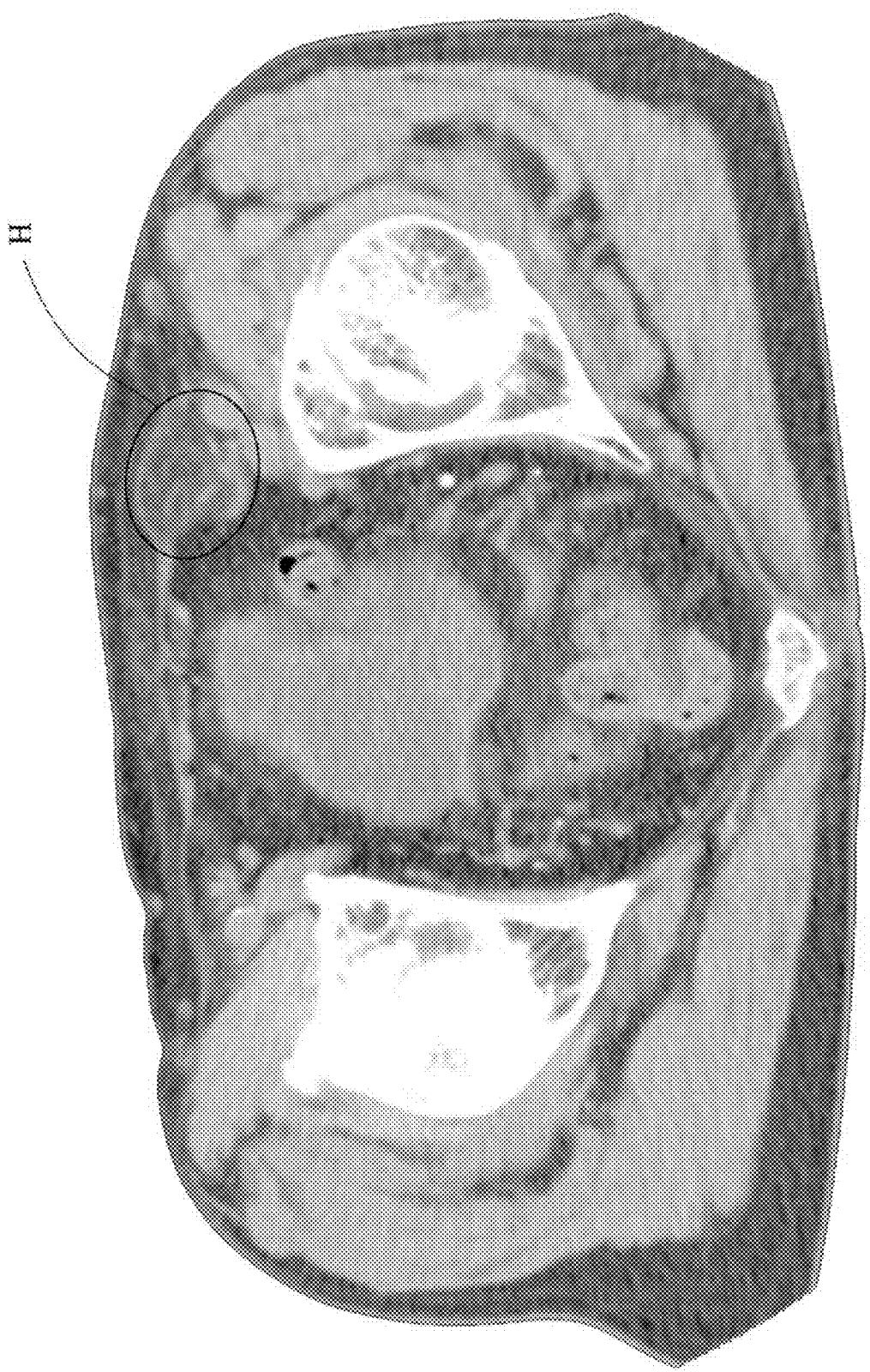
FIG. 1A is a cross-sectional computed tomography (CT) image of a patient with inguinal hernia, which is located in a region H marked by a dashed oval.
Figure 1B:
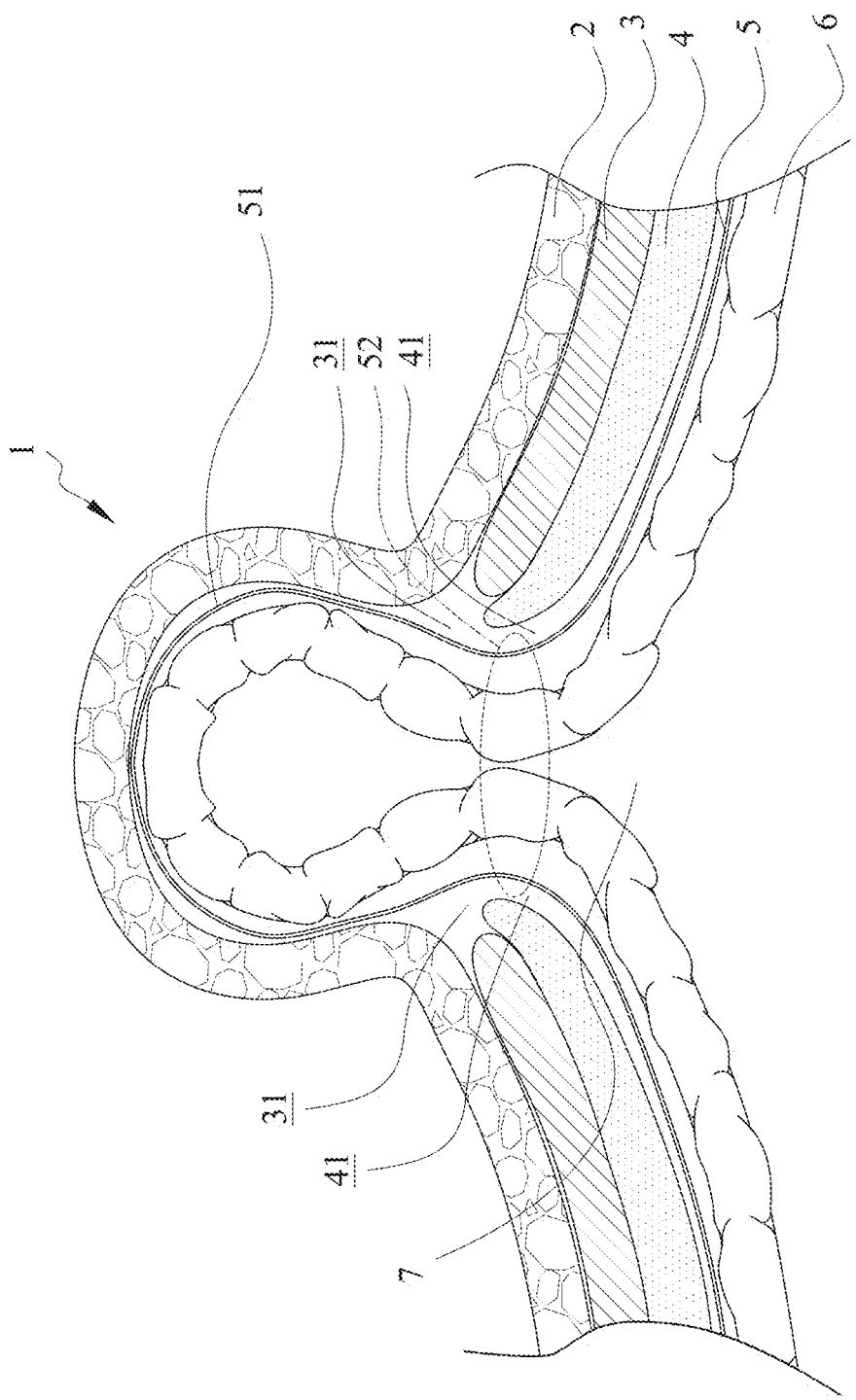
FIG. 1B is a schematic cross-sectional view illustrating inguinal hernia, a bulge in the skin layer resulted from the intestine protruding through a defect in the abdominal wall of a subject.

FIG. 1A is a cross-sectional computed tomography (CT) image of a patient with inguinal hernia, which is located in a region H marked by a dashed oval. FIG. 1B is a schematic cross-sectional view illustrating a defect 31 in the abdominal wall 3 of a subject suffered from inguinal hernia. Such defect 31 often causes internal organs such as the intestine 6 in the abdominal cavity 7 lined with a peritoneum 5 to protrude through both a preperitoneum 4 and the defect 31, resulting in a rupture 41 in the preperitoneum 4 underlying the defect 31 and a bulge 1 in the skin layer 2 above the defect 31. A part of the peritoneum 5 wrapped around the protruded intestine 6 forms a hernia sac 51 protruding though the defect 31 under the skin layer 2.

Figure 2:
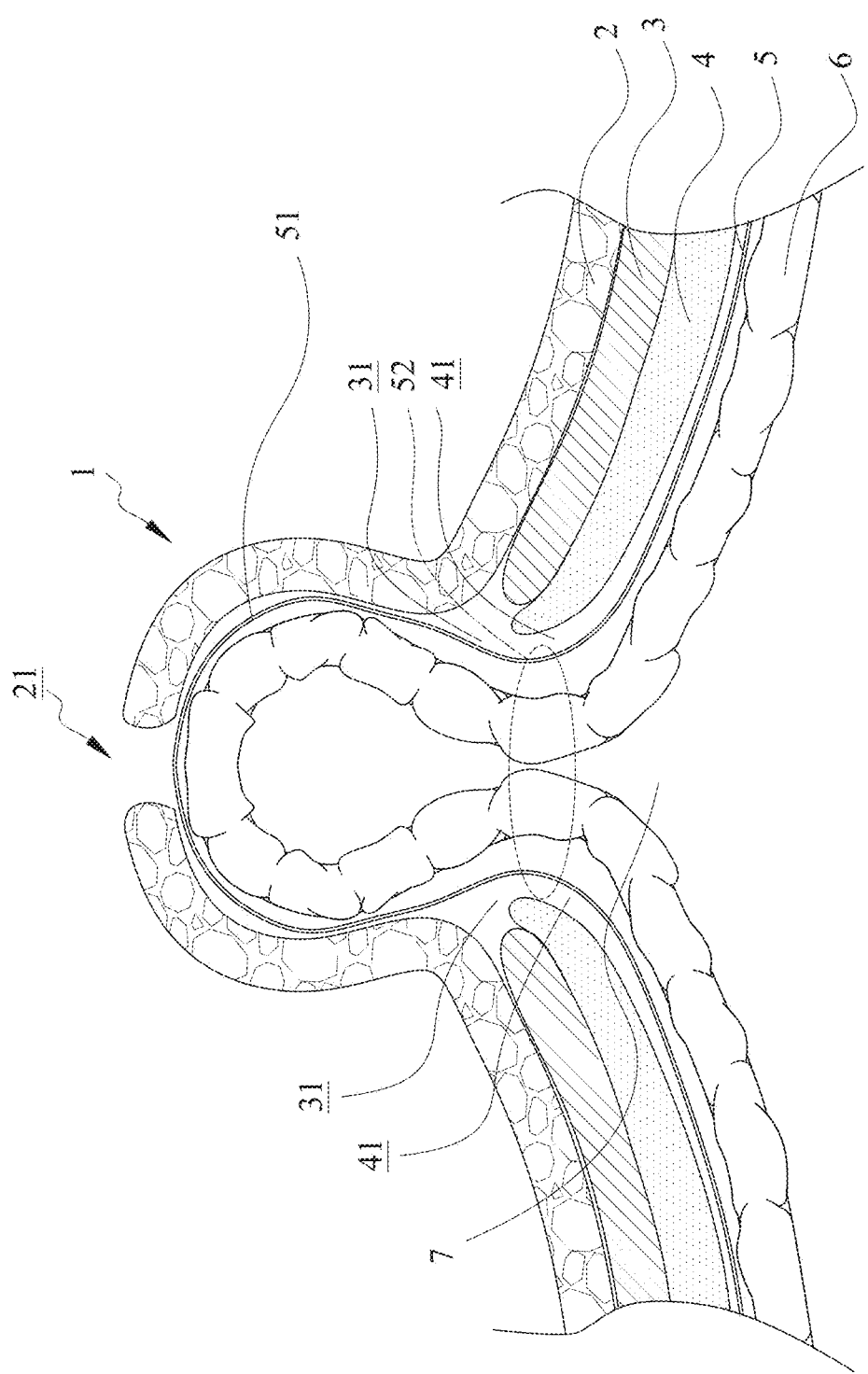
FIG. 2 is a cross-sectional view illustrating an incision made in the skin layer above the inguinal hernia defect in the abdominal wall.

Prior to a surgery for repairing the defect 31 in the abdominal wall 3 according to the method of the present invention, the subject suffered from inguinal hernia is given local anesthesia, for example, oral administration of diazepam. Next, as shown in FIG. 2, an incision 21 is made on the top surface of the bulge 1 and in the skin layer 2 above the defect 31. The length of the incision 21 is smaller than the diameter of the defect 31. Preferably, the length of the incision 21 is about 2-3 cm but not limited to this value. The depth of the incision varies depending on the location of the hernia sac 51, and it may extend over the thickness of the skin layer 2.

Figure 3:
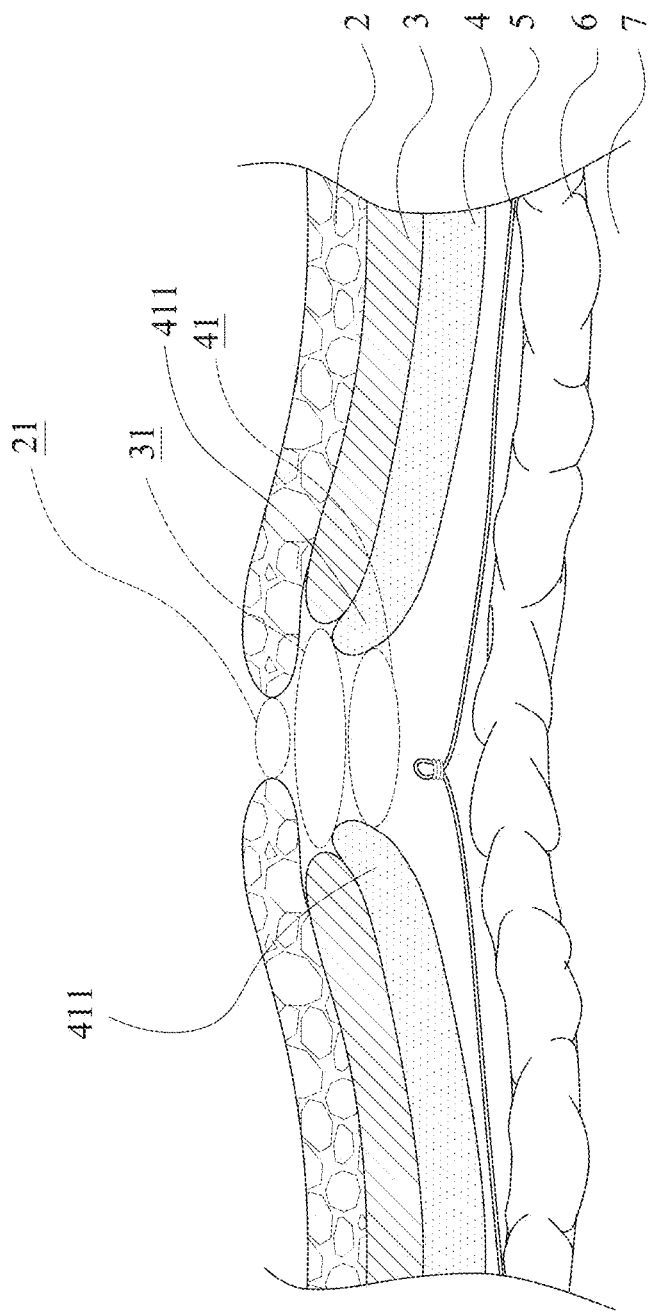
FIG. 3 is a cross-sectional view illustrating the intestine being repositioned into the abdominal cavity and a hernia sac being tied up and excised.

After the incision 21 is made, the hernia sac 51 in FIG. 2 is identified by visualization, and the protruded intestine 6 in the hernia sac 51 is pushed back into the abdominal cavity 7. The hernia sac 51 that remains protruded through the defect 31 may be tied up at its neck 52 near the rupture 41 in the preperitoneum 4 in FIG. 2 and be excised as shown in FIG. 3. Alternatively, the hernia sac 51 may also be pushed back into the abdominal wall.

Since hernia occurs when internal organs such as the intestine 6 protrudes through the defect 31 in the abdominal wall 3, a part of the preperitoneum 4 surrounding the rupture 41 is usually pulled upward by the protruded intestine 6 and becomes attached to the abdominal wall 3 around the defect 31, bringing about formation of a protruded region 411 in the preperitoneum 4, as shown in FIG. 3.

Figure 4:
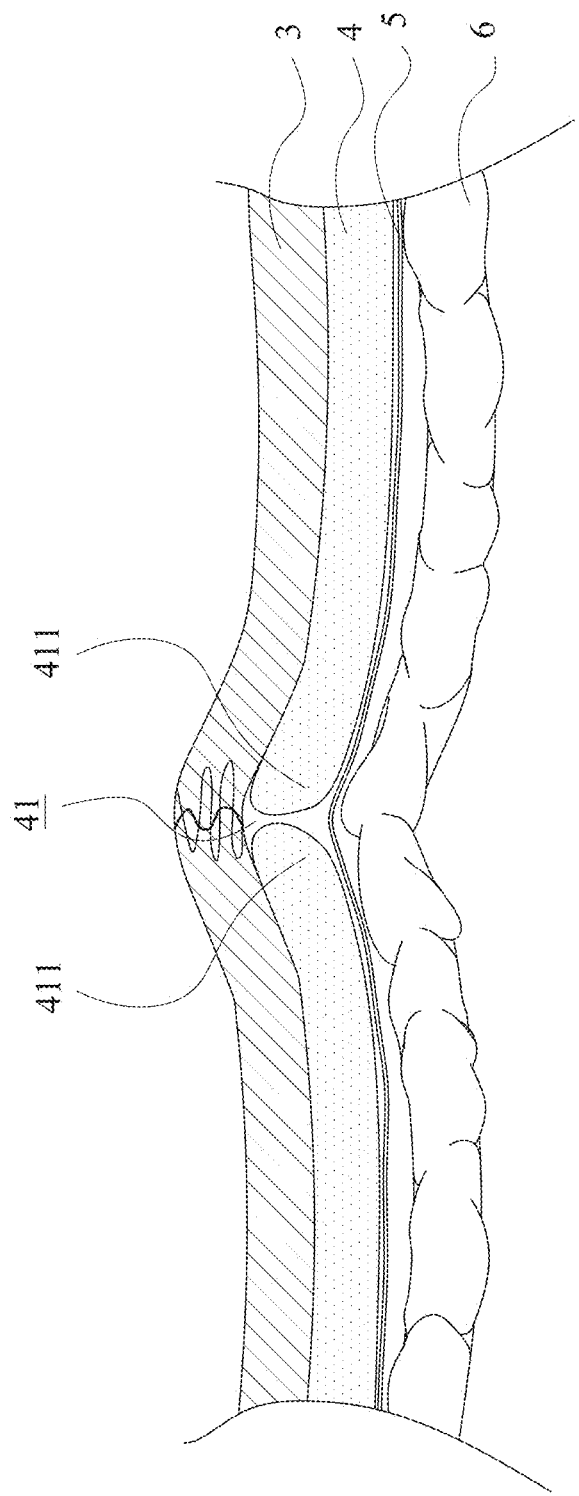
FIG. 4 is a cross-sectional view illustrating the small space between the abdominal wall and the preperitoneum and a protruded region of the preperitoneum exerting upward force on the repaired abdominal wall in the prior art.

According to the prior art, as shown in FIG. 4, the abdominal wall defect is repaired by simply suturing together two opposing edges of the abdominal wall defect while the protruded region 411 of the preperitoneum 4 is untreated. In this case, only small portions of the two opposing edges are not attached to the protruded region 411, and thus there is small space between the abdominal wall 3 and the preperitoneum 4 for the operation of suturing, resulting in a small distance between the borders of the suture across the two opposing edges and a sutured wound susceptible to tearing. Moreover, the protruded region 411 continuously exerts upward force on the repaired abdominal wall 3, and thus the repaired abdominal wall 3 is prone to pulling apart at the sutured wound, which leads to a higher recurrence rate of hernia.

To reduce this higher recurrence rate attributed to the untreated protruded region 411, the method of the present invention includes a step called "augmenting preperitoneum preparation (APP)" to separate the protruded region 411 of the preperitoneum from the abdominal wall 3 and flatten the protruded region 411 prior to reconstruction of the abdominal wall 3.

Figure 5:
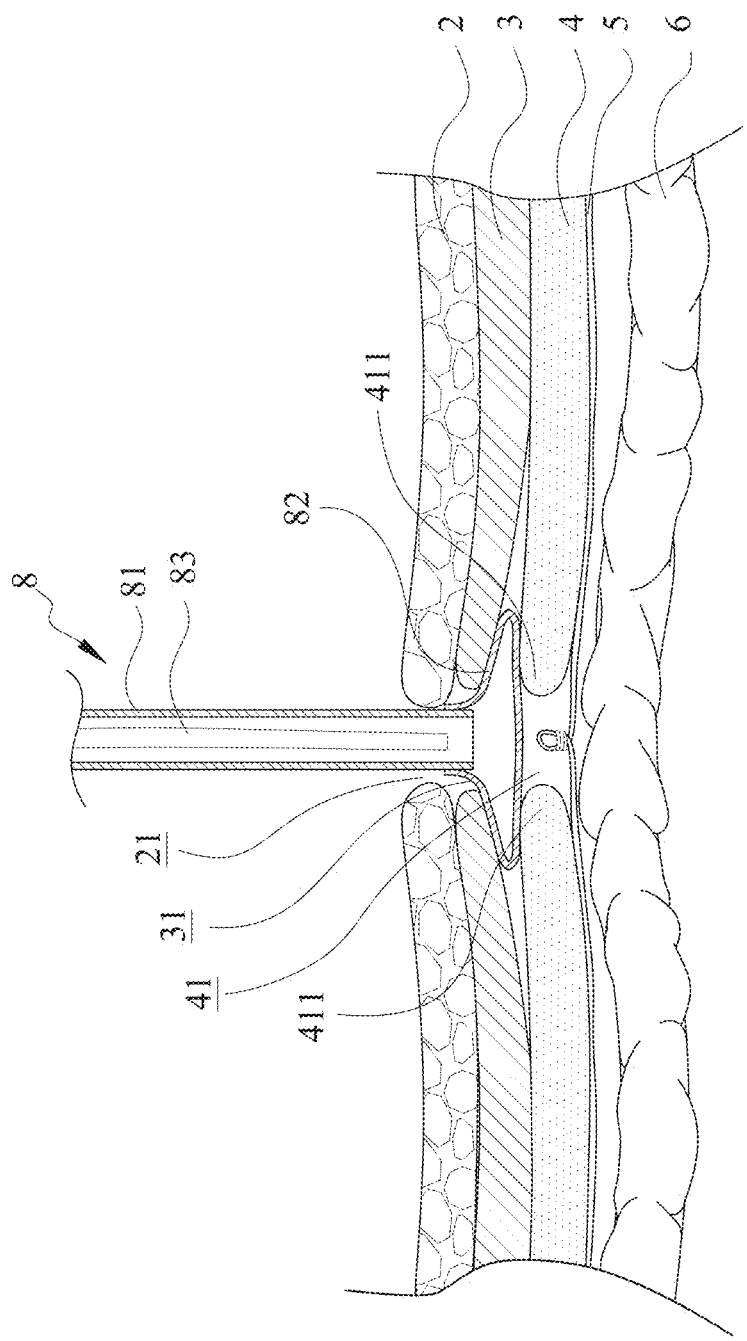
FIG. 5 is a cross-sectional view illustrating the protruded region of the preperitoneum having been flattened and separated from the abdominal wall using a surgical device including an inflatable sac in an expanded condition.

FIG. 5 illustrates the step of APP. As shown in FIG. 5, a surgical device 8 is introduced through the incision 21 in the skin layer 2 to reach the protruded region 411 of the preperitoneum 4. The surgical device 8 includes a main body 81 in the shape of a hollow tube, a deformable body such as an inflatable sac 82 conjugated to one end of the main body 81, and a monitoring element such as an endoscope 83 inside the main body 81. The inflatable sac 82 may have several protrusions extending radially from the center or it may be in any other shapes, for example, sphere, oval, and disc. Prior to access to the preperitoneum 4, the inflatable sac 82 is deflated for easy penetration through the single small incision 21, whereas it is in an expanded condition after being inflated at the site of the preperitoneum 4. In one embodiment of the present invention, the protruded region 411 of the preperitoneum 4 is identified with the endoscope 83 of the surgical device 8. Afterwards, the protruded region 411 is flattened and separated from the abdominal wall 3 with the inflatable sac 82 in the expanded condition, leading to a workable space between the abdominal wall 3 and the preperitoneum 4 for further operations. When no protruded region 411 is observed in the preperitoneum 4, the inflated sac 82 is deflated and the surgical device 8 is removed from the body.

Figure 6:
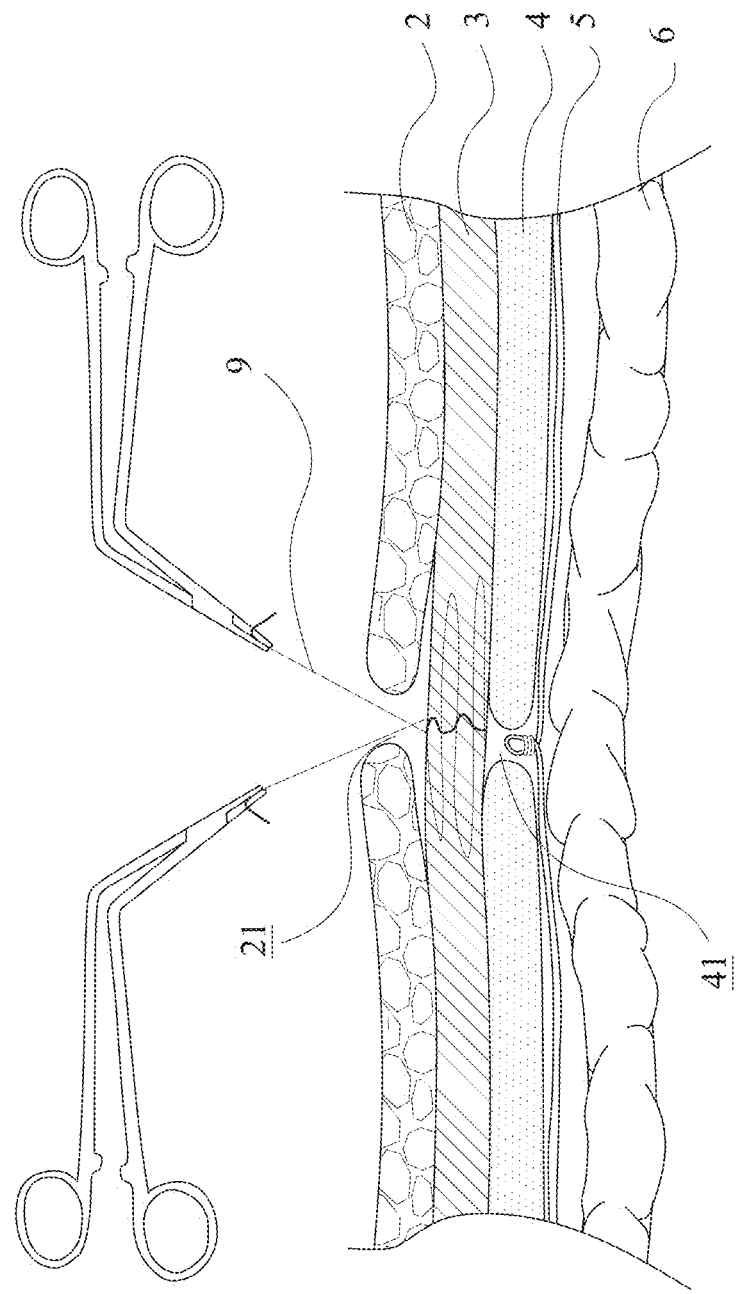
FIG. 6 is a cross-sectional view illustrating reconstruction of the abdominal wall by suturing continuously between tissues in the abdominal wall in an overlapping manner.

Next, the abdominal wall 3 is reconstructed. As shown in FIG. 6, a continuous suture 9 is used to sew edges of two adjacent tissues in the abdominal wall 3 in an overlapping manner to repair the defect 31 in FIG. 5. Since there are multiple tissues in the abdominal wall 3 around the defect 31, including ligament, tendon, fascia, etc., the step of suturing continuously between tissues is repeated multiple times to properly join two adjacent tissues at different locations in the abdominal wall 3. In the case of inguinal hernia repair in this example, Cooper's ligament is sutured to lower leaf of the inguinal ligament, the lower leaf of the inguinal ligament is sutured to a first part of the conjoint tendon, a second part of the conjoint tendon is sutured to upper leaf of the inguinal ligament, and a third part of the conjoint tendon is sutured to the external oblique fascia. Due to the overlapped tissues, the site of weakness in the abdominal wall 3 where hernia occurs is reinforced.

Figure 7:
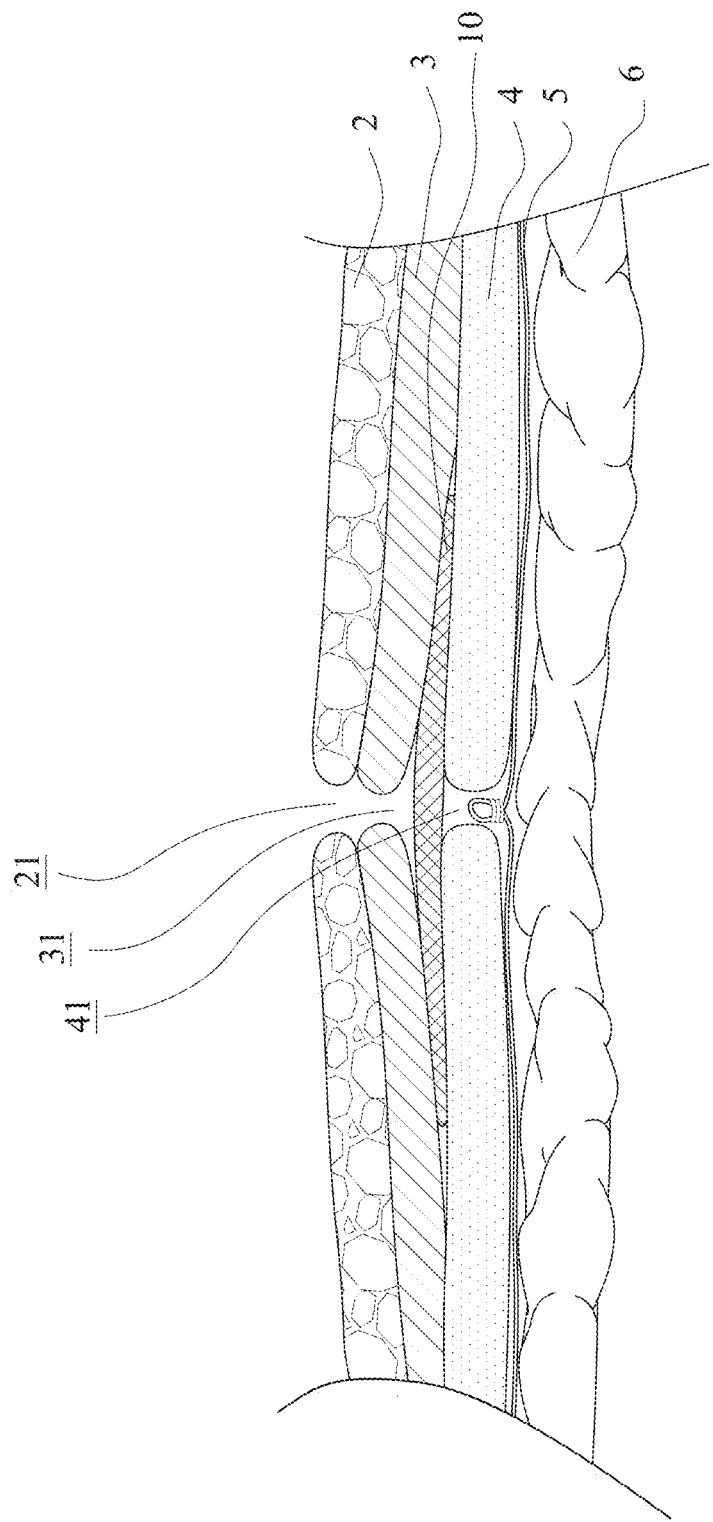
FIG. 7 is a cross-sectional view illustrating a surgical mesh being placed between the preperitoneum and the abdominal wall to reinforce the abdominal wall around the defect.

In another embodiment of the present invention, a surgical mesh or patch is used to repair the defect 31 when the abdominal wall 3 of a patient is diagnosed too thin for the abdominal wall reconstruction previously described. As shown in FIG. 7, a surgical mesh 10 is placed between the preperitoneum 4 and the abdominal wall 3 through the incision 21 in the skin layer 2 prior to suturing between tissues in the abdominal wall 3. Mesh placement may be accomplished by folding a surgical mesh 10 into a cone and then inserting it into the space between the preperitoneum 4 and the abdominal wall 3. Because the surgical mesh 10 is in contact with the abdominal wall 3, it may be sutured to the overlaying abdominal wall 3 around the defect 31 during abdominal wall reconstruction, which prevents its displacement from the site of the defect 31 and ensures reinforcement of the abdominal wall 3.

Figure 8:
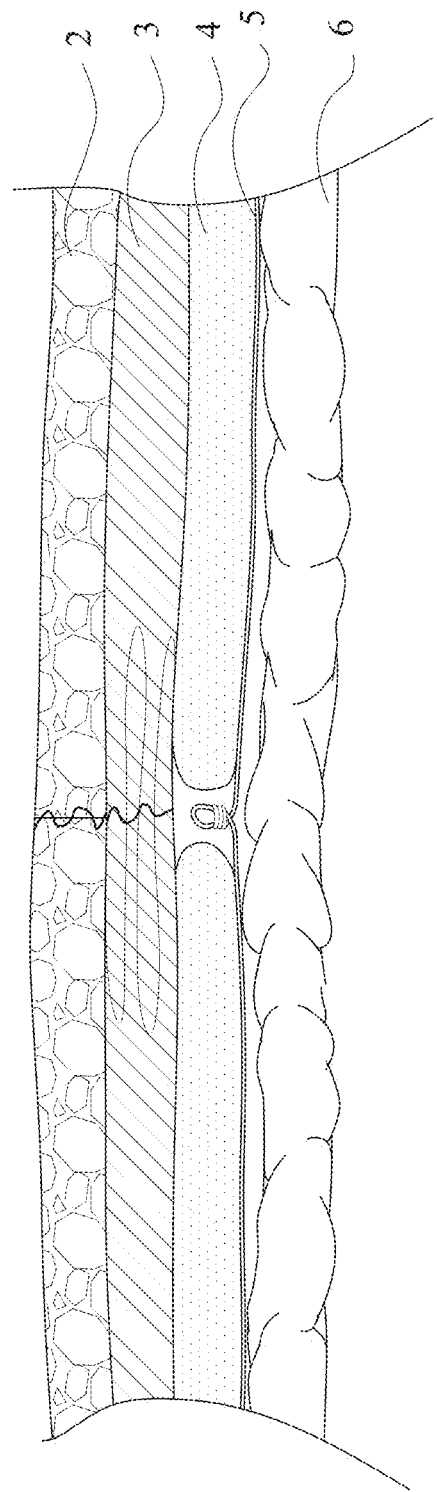
FIG. 8 is a cross-sectional view illustrating edges of the incision of the skin layer being sutured together.

The final step of the method of the present invention is to close the incision 21 in the skin layer 2 in FIG. 2 by suturing the edges of the incision 21 together. The repaired abdominal wall 3 with the closed skin layer 2 is shown in FIG. 8.

Compared with the prior art, the method of the present invention effectively lowers the recurrence rate of hernia for the following reasons. First, the APP step of the present invention flattens the protruded region 411 of the preperitoneum 4 in FIG. 5 prior to reconstruction of the abdominal wall 3, and thus the repaired abdominal wall 3, as shown in FIG. 8, is no longer pressed by the underlying preperitoneum 4.

Figure 9:
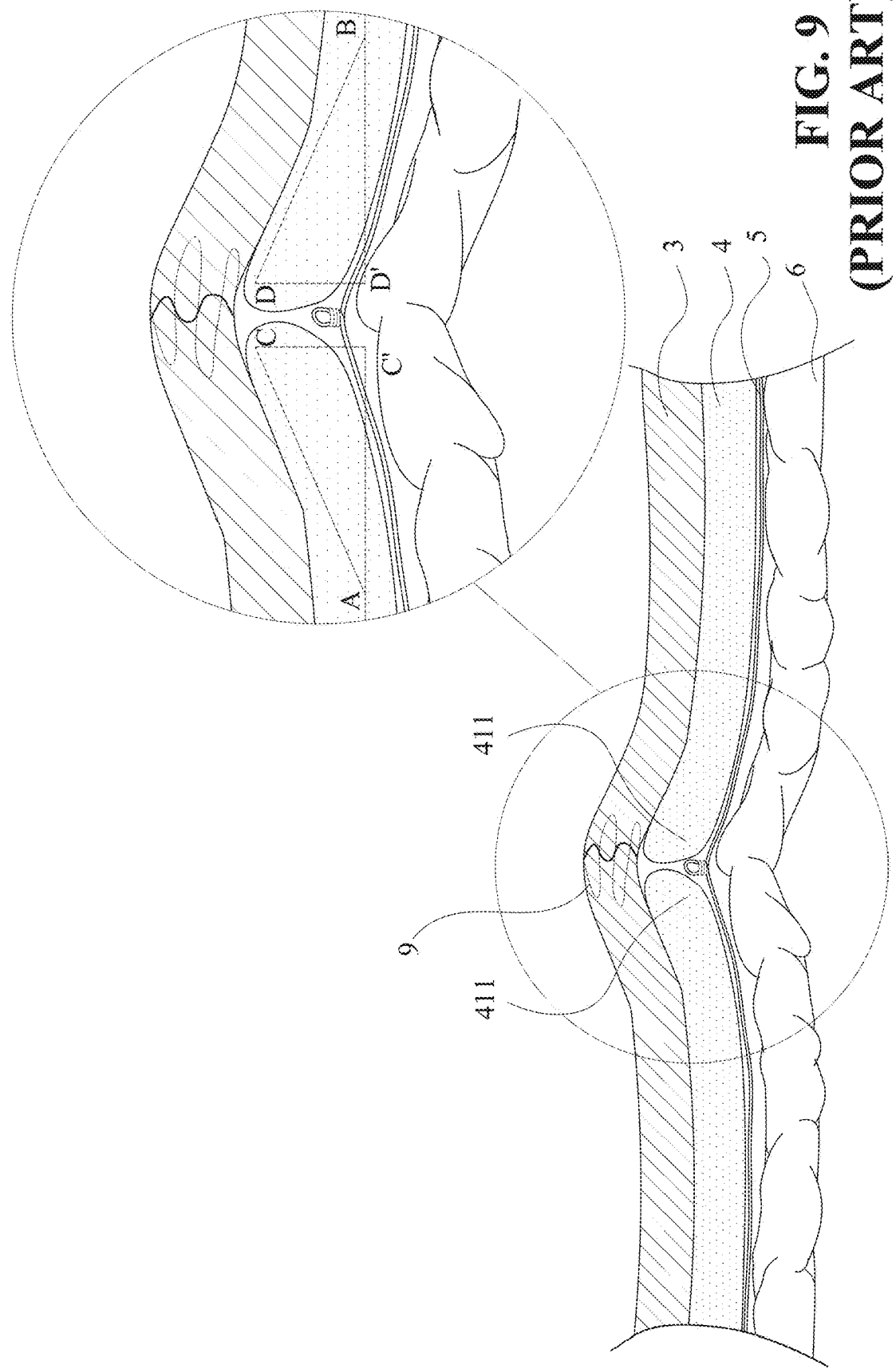
FIG. 9 is a cross-sectional view illustrating the small space between the abdominal wall and the preperitoneum and the longer cross-sectional length of the protruded region of the preperitoneum in the prior art.

Second, the APP step of the present invention creates a workable space between the abdominal wall 3 and the preperitoneum 4 for suturing together the edges of the abdominal wall defect, resulting in a greater distance between the borders of the suture 9 and a sutured wound less prone to tearing apart. The differences in the workable space and the distance between the borders of the suture 9 are illustrated in FIG. 9 and FIG. 10, which respectively show the suturing step of the conventional repair method and that of the method of the present invention. It is obvious that the workable space between the abdominal wall 3 and the preperitoneum 4 in FIG. 9 is much smaller than that in FIG. 10, and the distance between the borders of the suture 9 in FIG. 9 is also smaller than that in FIG. 10.

Third, the APP step of the present invention decreases prestress in the abdominal wall 3. Geometrically, the protruded region 411 of the preperitoneum 4 has an up-tilted configuration and a longer cross-sectional length. As shown in FIG. 9, the cross-sectional length of the protruded region 411 is the sum of the lengths of line AC and line BD. According to the conventional repair method, the tissues in the abdominal wall 3 have to be held together along the extended protruded region 411 by greater force to come close for suturing. Therefore, there is a higher prestress in the abdominal wall 3, leading to a sutured wound more easily to tear. However, when the step of APP is applied and the protruded region 411 in FIG. 5 is flattened and retracted, the resulting cross-sectional length of this region would reduce to the sum of the lengths of line AC' and line BD' in FIG. 10. In this case, less force is needed to pull the tissues in the abdominal wall 3 for suturing, and the prestress in the abdominal wall 3 is decreased, leading to a sutured wound less susceptible to tearing.

In conclusion, the method of repairing a defect in the abdominal wall of the present invention includes the essential steps of flattening the protruded region of the preperitoneum and separating the protruded region of the preperitoneum from the abdominal wall, and suturing continuously between tissues in the abdominal wall in an overlapping manner for abdominal wall reconstruction. The method of the preset invention not only repairs the defect in the abdominal wall but also reduces the tension of the reconstructed abdominal wall though a single small incision in the body of a subject. The average recurrence rate of inguinal hernia after operations using the method of the present invention is about 0.2% for over 2000 patients, which is much lower than the recurrence rates after conventional operations. According to the statistics, the recurrence rates of inguinal hernia after Bassini repair, Shouldice repair, Lichtenstein repair, TEP repair, and TAPP repair are about 5-15%, 0.5-1%, 2-3%, 2-7%, and 3-7%, respectively.

The method of repairing a defect in an abdominal wall of a subject provided herein is applicable and valuable. The present invention has been described with reference to the above preferred embodiments. However, it will be apparent to those skilled in the art that modifications and changes in form and detail may be made without departing from the scope of the present invention defined by the appended claims.

What is claimed is:

1. A method of repairing a defect in an abdominal wall of a subject, comprising the steps of:
   (a) making an incision through a skin layer above the defect in the abdominal wall, wherein the incision is smaller than the defect;
   (b) introducing a surgical device through the incision to reach a preperitoneum underlying the abdominal wall around the defect, wherein the surgical device comprises a deformable body;
   (c) using the surgical device to identify a protruded region of the preperitoneum extending towards the abdominal wall around the defect; and
   (d) flattening the protruded region of the preperitoneum and separating the protruded region of the preperitoneum from the abdominal wall with the deformable body in an expanded condition.

2. The method of claim 1, wherein in step (a) the incision is about 2-3 cm in length.

3. The method of claim 1, wherein the subject is given local anesthesia prior to step (a).

4. The method of claim 1, wherein the surgical device further comprises a monitoring element.

5. The method of claim 4, wherein the monitoring element is an endoscope.

6. The method of claim 1, wherein the deformable body is an inflatable sac.

7. The method of claim 1, wherein the defect is a hernia defect.

8. The method of claim 7, further comprising the step of excising a hernia sac within the defect prior to step (b).

9. The method of claim 7, further comprising the step of suturing continuously between a plurality of tissues in proximity to the defect in an overlapping manner to reconstruct the abdominal wall after step (d).

10. The method of claim 9, further comprising the step of placing a surgical mesh between the abdominal wall and the flattened preperitoneum and suturing the surgical mesh to the abdominal wall.

11. The method of claim 7, further comprising the step of closing the incision of the skin layer.

* * * * *